United States Patent
Carr

(10) Patent No.: US 8,389,274 B2
(45) Date of Patent: Mar. 5, 2013

(54) METHOD AND APPARATUS FOR THE NON-INVASIVE MONITORING OF GAS EXCHANGE BY BIOLOGICAL MATERIAL

(75) Inventor: Tony Carr, Bedfordshire (GB)

(73) Assignee: Bactest Limited (GB)

( * ) Notice: Subject to any disclaimer, the term of this patent is extended or adjusted under 35 U.S.C. 154(b) by 0 days.

(21) Appl. No.: 13/102,445

(22) Filed: May 6, 2011

(65) Prior Publication Data

US 2011/0312021 A1 Dec. 22, 2011

Related U.S. Application Data

(63) Continuation of application No. 10/508,081, filed as application No. PCT/GB03/01179 on Mar. 14, 2003, now abandoned.

(30) Foreign Application Priority Data

Mar. 16, 2002 (GB) .................................. 0206275.0

(51) Int. Cl.
   *C12M 1/34* (2006.01)
(52) U.S. Cl. .................... 435/287.5; 435/34; 435/287.1; 73/52
(58) Field of Classification Search ............ 435/34, 435/287.1, 5, 287.5; 436/48; 422/64, 186.25, 422/208, 226, 295, 296, 657; 73/52, 1.35, 73/1.71, 19.05, 23.27, 23.29, 30.02, 54.09, 73/54.14; 43/715; 250/360.1; 356/400, 356/482, 493, 496, 630; 366/199, 224, 244, 366/247, 249, 273, 274, 325.6, 325.7, 325.8, 366/325.92
See application file for complete search history.

(56) References Cited

U.S. PATENT DOCUMENTS

| | | | |
|---|---|---|---|
| 2,321,293 A | 6/1943 | Hassler |
| 2,917,372 A | 12/1959 | Wallin |
| 3,764,836 A | 10/1973 | Bender et al. |
| 4,152,213 A | 5/1979 | Ahnell |
| 4,226,124 A | 10/1980 | Kersten |
| 4,641,533 A | 2/1987 | Mueller et al. |
| 4,773,269 A | 9/1988 | Knecht et al. |
| 4,884,451 A | 12/1989 | Schulze |
| 4,952,498 A | 8/1990 | Waters |
| 5,047,331 A | 9/1991 | Swaine et al. |
| 5,051,360 A | 9/1991 | Waters |
| 5,232,839 A | 8/1993 | Eden et al. |
| 5,426,024 A | 6/1995 | Flores-Cotera et al. |
| 5,591,171 A | 1/1997 | Brown |

(Continued)

FOREIGN PATENT DOCUMENTS

| EP | 0278341 | 8/1988 |
|---|---|---|
| EP | 0374858 | 6/1990 |

(Continued)

*Primary Examiner* — Michael Hobbs
(74) *Attorney, Agent, or Firm* — Perkins Coie LLP

(57) ABSTRACT

The invention provides an indirect pressure sensing system for non-invasive measurement of primary pressure in a sealed container, which communicates primary pressure changes from within the container, via a flexible diaphragm, to a secondary chamber wherein there is a defined relationship between the primary and secondary pressures, which enables a pressure sensor in the secondary chamber to generate a signal representing primary pressure in the sealed container, but to remain isolated from the contents of the sealed container. The pressure sensor can provide electrical outputs representing the pressure detected, and the outputs are fed to data processing means capable of producing a measurement of primary pressure. The system can have a liquid culture of cellular material (eg. micro organisms, plant tissue cells, animal cells etc) partially filling the container, whereby the metabolism and/or growth of cellular material causes gas exchanges between liquid and headspace, which can result in primary pressure changes.

27 Claims, 11 Drawing Sheets

U.S. PATENT DOCUMENTS

| | | | |
|---|---|---|---|
| 5,770,153 A | 6/1998 | Wagner | |
| 5,863,752 A * | 1/1999 | Court et al. | 435/34 |
| 5,863,753 A | 1/1999 | Haugland et al. | |
| 5,869,766 A | 2/1999 | Cucci et al. | |
| 5,888,825 A | 3/1999 | Carr et al. | |
| 5,976,824 A | 11/1999 | Gordon | |
| 6,043,049 A | 3/2000 | Lemonnier | |
| 6,258,593 B1 | 7/2001 | Schembri et al. | |
| 2002/0090736 A1 | 7/2002 | Ulin | |
| 2002/0142454 A1 | 10/2002 | Cracauer et al. | |
| 2004/0256769 A1 | 12/2004 | Walter | |
| 2005/0170497 A1 | 8/2005 | Carr | |

FOREIGN PATENT DOCUMENTS

| | | |
|---|---|---|
| WO | WO 94/02238 | 2/1994 |
| WO | WO 94/19421 | 9/1994 |
| WO | WO 00/65984 | 11/2000 |

* cited by examiner

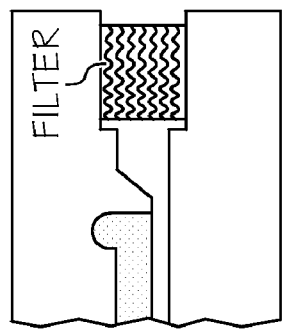
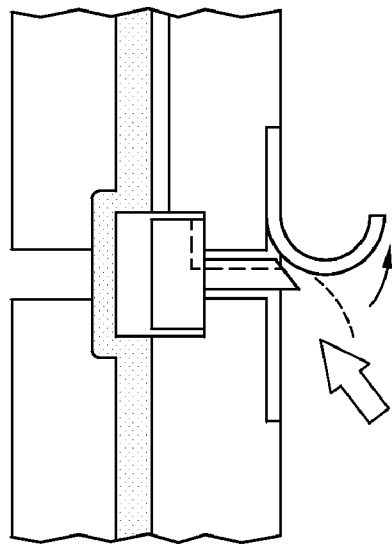
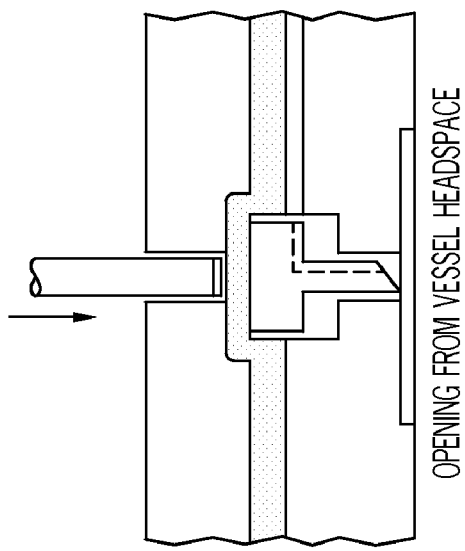
FIG. 4C
FIG. 4B
FIG. 4A

FIG. 5A  OPENING FROM VESSEL HEADSPACE

METHOD AND APPARATUS FOR THE NON-INVASIVE MONITORING OF GAS EXCHANGE BY BIOLOGICAL MATERIAL

This application is a continuation of U.S. application Ser. No. 10/508,081 filed Feb. 15, 2005 now abandoned, which is 371 of International App. No. PCT/GB03/01179 filed Mar. 14, 2003. This application also claims priority to GB 0206275.0 filed Mar. 16, 2002, which is hereby incorporated by reference. The entire contents of the above-identified applications are hereby incorporated by reference.

FIELD OF THE INVENTION

Methods for monitoring biological activity are particularly valuable in laboratory tests carried out in sealed containers. Unlike open processes (for the conversion of raw materials to valuable end products), the laboratory test generates information about the detection or monitoring of biological activities. Containment is a critical feature both for safety reasons (where the contents are unknown and potentially dangerous) and as a barrier to contamination (where the test outcome could be invalidated by an unknown contaminant to which the result may be attributable).

Numerous laboratory tests involve cells or organelles (this includes bacteria, algae, plant and animal cells, protozoa and cell components) in suspension cultures.

Respiration is a key, central feature of metabolism which can monitor activity levels, and increase to reflect growth/multiplication of cells. There are commercially available systems that detect carbon dioxide production, or oxygen depletion, by optical monitoring of a gel coating at the base of a culture bottle. These methods are limited to the specific gas detectable by the chemistry used, and, obviously, give no indication of the prevailing pressure in the bottle. In some test situations certain species of bacteria can generate appreciable positive pressures. Any attempt to sample such cultures could prove hazardous due to the release of aerosols. Gas exchange is a good, general-purpose measurement parameter and in this context headspace pressure is an excellent monitoring system. Blood culture instruments described in U.S. Pat. No. 5,672,484 and WO9521241 involve the use of individual pressure sensors connected to individual culture bottles, with a protective filter interposed. This is effective as a measurement system but is unavoidably invasive, due to the use of a hypodermic needle in the connection assembly. The method described in WO9303178 is based on laser height measurement to measure pressure in terms of distension of a large area septum. While non-invasive, the method involves a relatively expensive, high sensitivity sensor. This is only practical when a mechanism is used to move the sensor over the bottles.

The current invention recognises that a sealed container, partially filled with liquid can experience gas exchanges, which results in pressure variation in the headspace. Pressure variation could be due to temperature effects, but these can be prevented by good temperature control, which is relatively easy to achieve. Should the container include any significant area of flexible material then barometric pressure changes can exert an influence, however, this is not so in a rigid container. Ideally all pressure variations should be a direct reflection of activity levels in the biological component of the liquid phase.

This invention includes a primary sealed container with a closure incorporating a flexible diaphragm closure across a secondary chamber. One side of the diaphragm is in contact with the gas and liquid phases of the main chamber so that the diaphragm forms a barrier isolating the secondary chamber and sensor from the main vessel contents.

Pressure variations in the main container headspace are sensed by a pressure transducer fitted to the secondary chamber.

This system operates as a respirometer monitoring gas exchange by biological preparations. The flexible diaphragm is a sterility barrier. The liquid phase and any active cells can only exchange gasses with the main headspace (25 mL in this case). In terms of pressure however the biological preparation has access to the combined headspace volume of 30 mL. approximately. The monitoring system operates at or around atmospheric pressure and changes are normally in the order of 100 millibars positive or negative, about atmospheric pressure.

Very small changes of say 50 millibars are significant and in some cases rate of change measurement are valuable.

Sensitivity, sterility and impermeability are essential, in addition the material of the diaphragm must be bio-compatible.

The characteristics of the diaphragm (for example, diameter, elasticity and thickness) will attenuate the extent of the variation, but the relationship between 'primary' and 'secondary' pressures is simple.

The majority of test containers in commercially available systems are based on a bottle or tube, usually of glass. This invention provides a container, which is itself purpose designed as a disposable, single use item, for use with the apparatus of the invention. The crux of any method based on gas exchange is to ensure adequate interaction between the liquid and gas phases. Primarily for this reason, the device includes a major feature intended to promote efficient gas exchange. Since the pressure itself is monitored, the design of the vessel leaves scope to add a series of additional features, each intended to provide management of vessel pressure at various stages of a test procedure.

Integral filters ensure that any gas exchange with the environment does not compromise the levels of containment. In blood culture applications these additional facilities are unique, and provide an improved level of safety. This is an attractive feature where a blood sample may include virus such as hepatitis and/or HIV, in addition to any bacterial infection.

The invention provides the facility for monitoring gas exchange, and this can be applied in a number of ways. For example, the presence of micro-organisms at low levels can be demonstrated by the addition of a sample to a suitable growth media, followed by a period of incubation. The viable count will rise, and activity will be detected. This detection capability is applicable to blood, serum, spinal fluid and aspirates. The monitoring of activity levels can be applied to specific species or, indeed, complex mixtures (e.g. Activated Sludge). Tests can monitor both enhancement and inhibition of activity. In this way, potential nutrients, preservatives or pollutants are examined for any influence on activity levels, with the test apparatus performing the role of a respirometer.

In a more specialised form, a chemical carbon dioxide scavenger (KOH) creates an oxygen depletion measurement and, hence, a means to determine the Biological Oxygen Demand (BOD) of, say, a water sample.

It is noted that growth media formulations should be matched to the applications, but with an emphasis on promoting gas exchange.

The instrument could take many forms, but must control mixing effectively, through a range of possible regimes, and maintain precise control of temperature. Signals representing pressure are transferred from the sensor, to an Analogue to Digital convertor, and then to a microprocessor where data can be processed, generally using simple algorithms to calculate the rates and significance of changes. Decisions and conclusions can be displayed, or relayed to a PC. Instrument capacity could be small or scaled up as multiples of the small basic unit. In a simple form the unit would process one sample, but it would be more typical to have a basic unit that processes two disposables at a time (typically one aerobic/ one anaerobic). This is an unusually low cost package of minimal complexity, very portable, and with virtually no service requirement.

In a blood culture context, the basic unit could process aerobic/anaerobic samples from the same patient, thus providing a self contained, low cost system with no need for large, high capacity machines of major capital cost that would require service back-up.

The enhanced level of containment and safety features are of value in the testing of high risk samples, even to the extent of locating units close to the sampling facility. In the event of the unit becoming unsafe, e.g. if leakage has occurred, either the test vessel and its silo can be removed, or the complete unit subjected to sterilisation and disposal.

SUMMARY OF THE INVENTION

The present invention describes a method and instrument for detecting and monitoring gas exchange in biological preparations. The system is based on the measurement of pressure in a sealed container, partially filled with liquid. Components of the liquid can give rise to gas exchanges between the liquid and container headspace, resulting in primary pressure variations. The sealed container includes a flexible diaphragm at the boundary between a main headspace and a closed secondary chamber that contains compressible gas and a direct connection to an electronic pressure sensor. There is a simple relationship between primary and secondary pressures, where the sensor measures the latter.

The complete system is divided into a single use component and a durable instrument. Single use, disposable containers provide containment during the test, followed by sterilisation and disposal after use. The unique design of the container described here is intended to provide optimum conditions for gas exchange. Furthermore there are several optional features that significantly increase the level of control over vessel pressures at the various stages of conducting a test. These features enhance the safety and containment aspects of the design. The present invention gives rise to the container design, which is directly linked to the functionalities required in practical applications of the system.

The instrument is physically compact, housing one, or more normally two, of the single use containers. Using micro or process controllers, the mixing, measurement and temperature control functions are supervised in parallel with data processing to identify significant pressure changes. No part of the instrument comes into contact with biological material. The regions which house the disposables, for test duration, provide precise temperature control but also act as a bund or silo for containment purposes.

In the unlikely event of spillage, the silo and contents can be removed, rendered safe and disposed of although this sacrifices part of the instrument, it is a particularly attractive safety feature.

The ability to indirectly monitor pressure, plus a number of key safety/containment features, can be usefully combined in applications involving the detection of micro-organisms. In particular, blood culture, as provided by hospital laboratories, is described below as a typical, routine application for this invention.

BRIEF DESCRIPTION OF THE DRAWINGS

FIGS. 4A to 4C: A single action valve for connection permanently between headspace and the sensor system. Operation of the valve is indirect, via a membrane barrier, using manual pressure to perforate foil seal. FIG. 4A shows the opening from vessel headspace while the valve is closed; 4B shows open frangible seal and perforated gas flow; and 4C shows filter in opening to the atmosphere.

FIGS. 5A to 5C: A multiple action valve, again indirect via a membrane, but only open when activated and thus providing momentary connection of headspace to atmosphere via a filter. FIG. 5A shows the opening from vessel headspace while the valve is closed; 5B shows open system and gas flow; and 5C shows filter at the opening to the atmosphere.

in FIG. 6B a shaft with increased surface area, for optional elution of compounds coated on surface; in FIG. 6C a coated shaft, potentially offering an improved growth substrate for cells; and in FIG. 6D a hollow mesh carrier, either to expose media to supplementary compounds or to remove inhibitors such as antibiotics by retention in resins contained within.

in FIG. 7B paddle structures which are increased volume versions of the paddle structures of FIG. 7A to increase the interfacial area; in FIG. 7C paddle structures which are increased volume versions of the paddle structures of FIG. 7A but with drainage holes to allow trickling of media back into the main volume; and in FIG. 7D a paddle structure comprising a cylindrical carrier with a multitude of pockets.

DETAILED DESCRIPTION OF THE INVENTION

Figure 1:
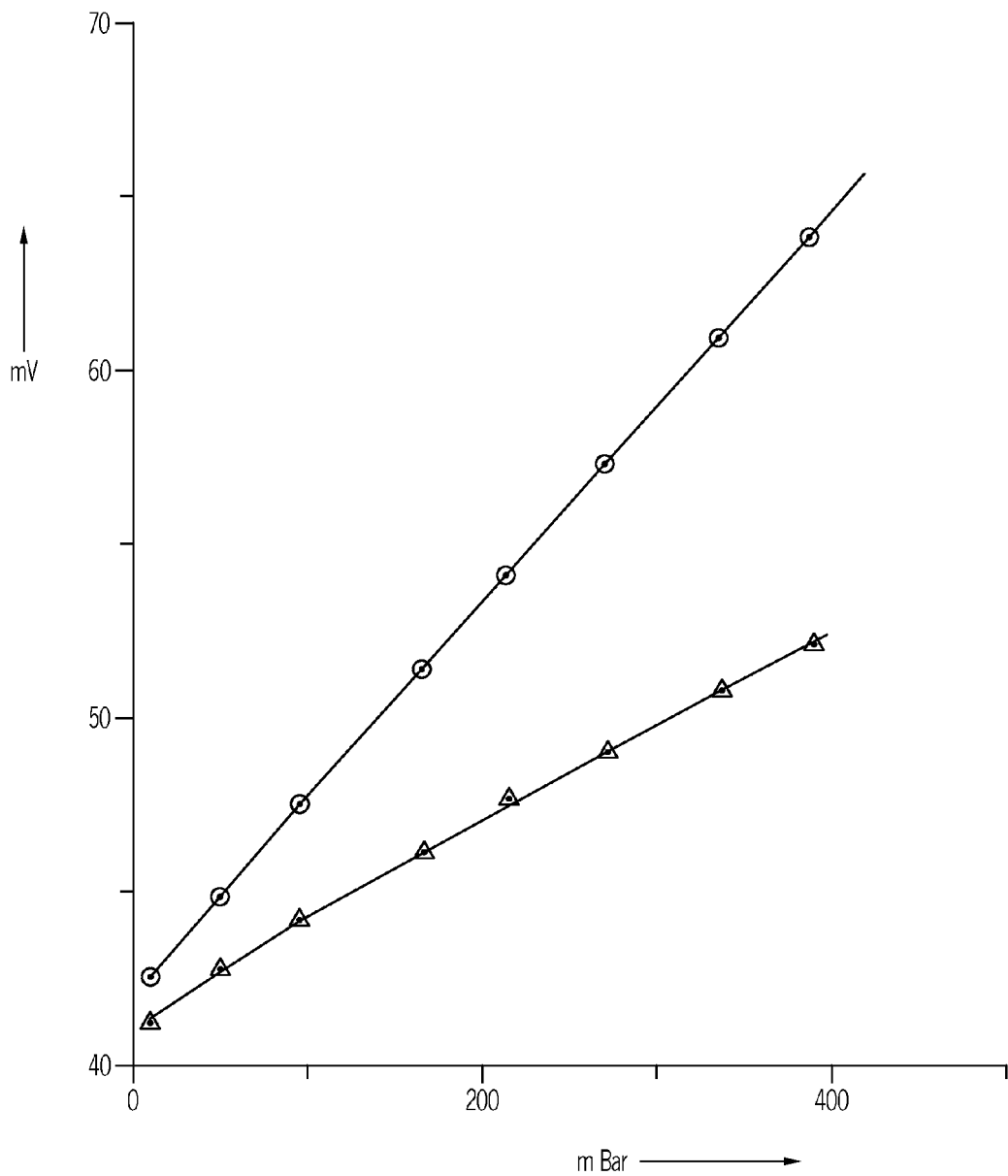
FIG. 1: Graph comparing primary pressure sensor reading with those from a secondary pressure sensor, over a range of known pressure values. In this experiment transfer of pressure was via a 30 mm diameter/0.8 mm thickness Butyl Rubber. Sensor readings are recorded in millivolts, with actual pressure valves in mbar (using a fully calibrated Druck meter). The traces of primary values are marked with circles, and the corresponding secondary pressures marked as triangles.
Figure 2A:
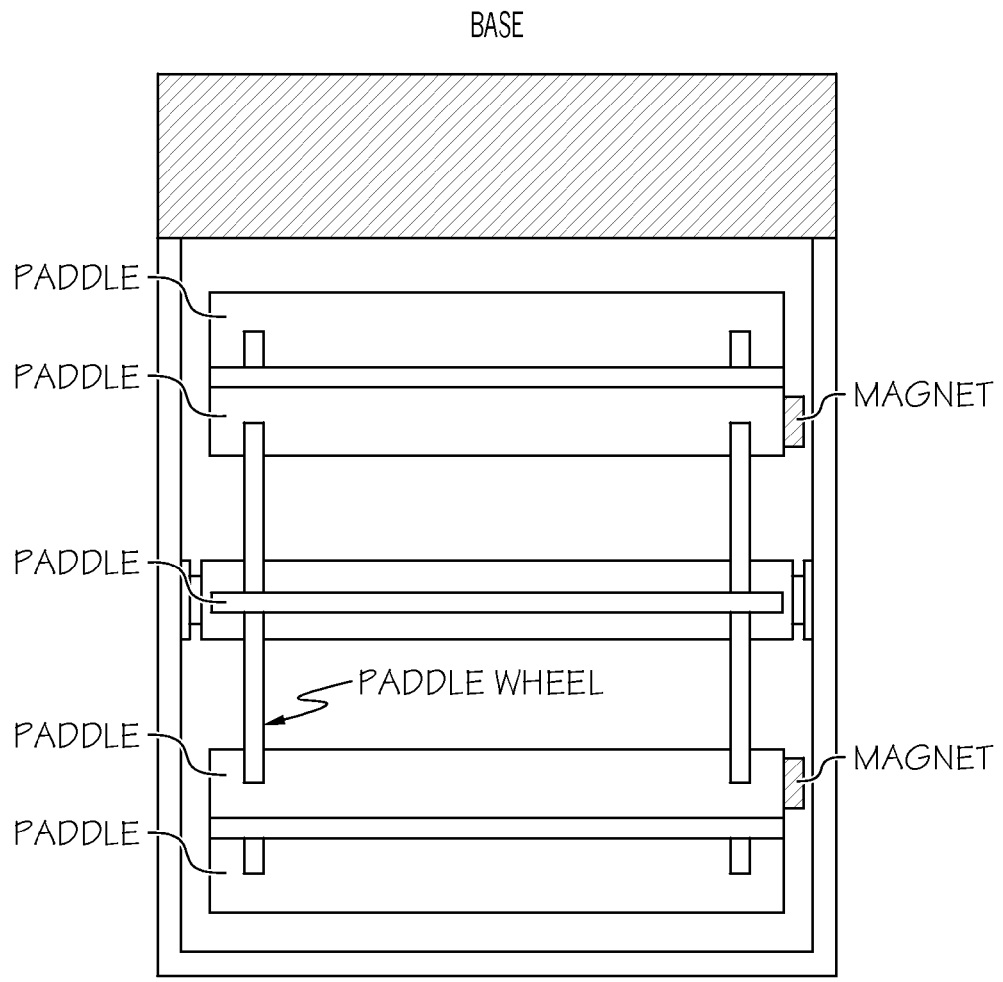
FIGS. 2A to 2C: These show, respectively, base (FIG. 2A), side (FIG. 2B) and front (FIG. 2C) views of a single use disposable container for the apparatus showing the paddle wheel and its drive magnets on the right hand side and the injection port closed with a tamper evident, detachable lid. It should be noted that the lid and closure have deliberate asymmetrical features, this ensures correct orientation on loading and hence fail/safe magnetic coupling of the drive system.
Figure 2B:
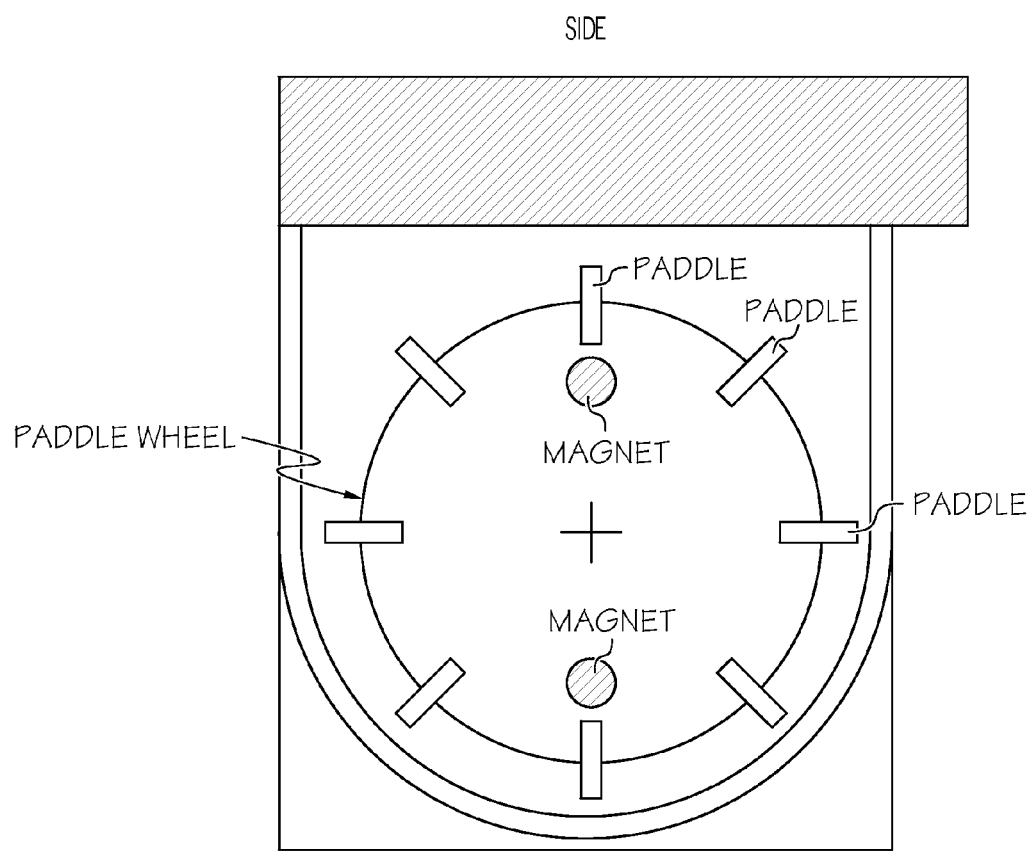
Figure 2C:
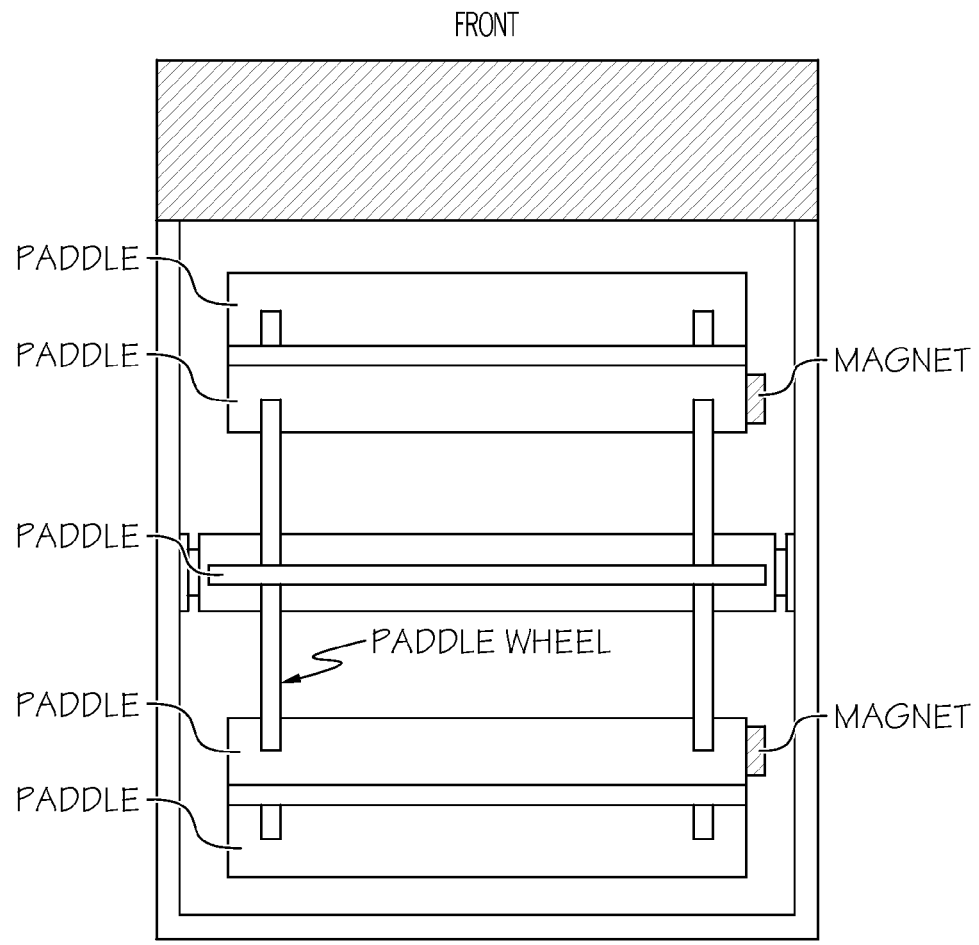
Figure 3:
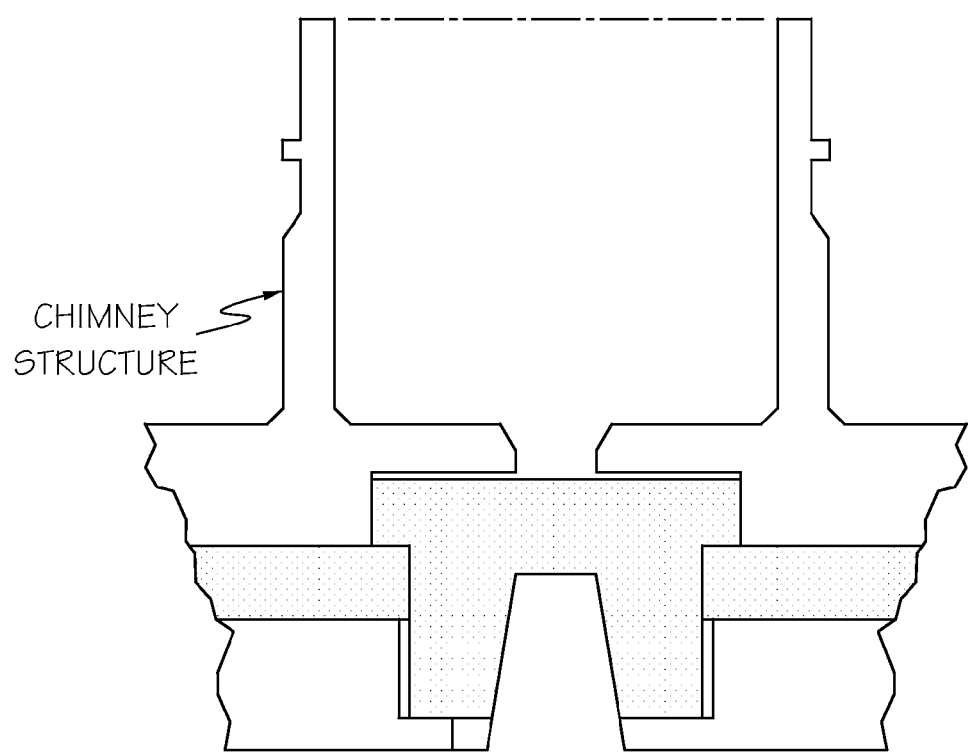
FIG. 3: The injection port, for addition of samples and removal of subcultures using syringes. The port is expected to protect against needle-stick issues by virtue of the large diameter "chimney-like" structure.
Figure 5B:
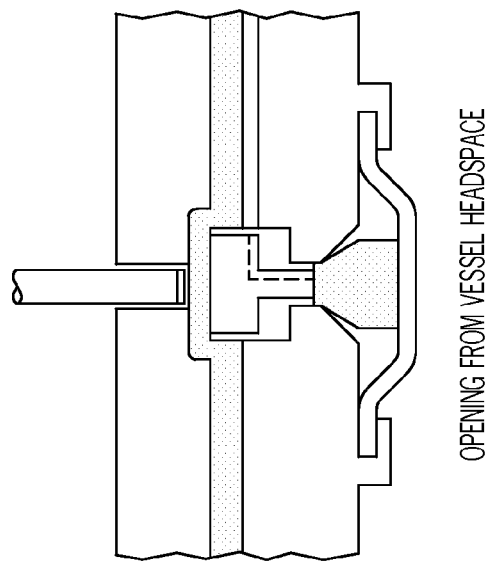
Figure 5B:
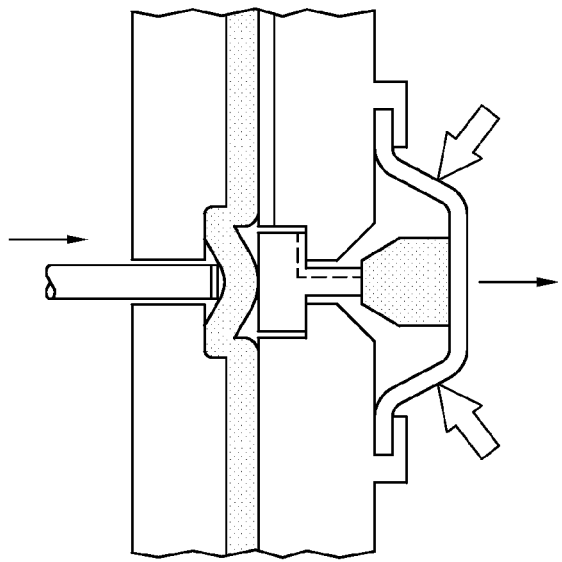
Figure 5C:
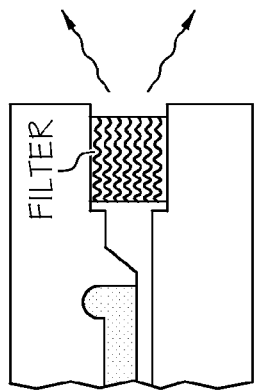
Figure 6A:
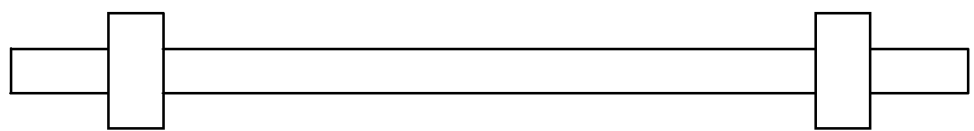
FIGS. 6A to 6D: These show side views of paddle wheel shafts illustrating options for functional features on shafts through the paddle wheel centre axis and showing, respectively, in FIG. 6A a standard shaft.
Figure 6B:
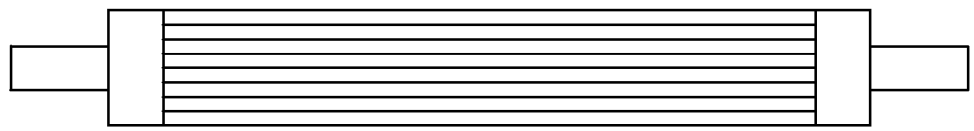
Figure 6C:
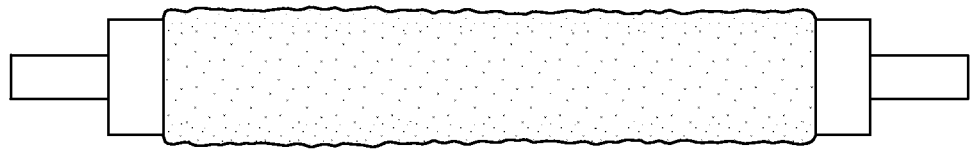
Figure 6D:
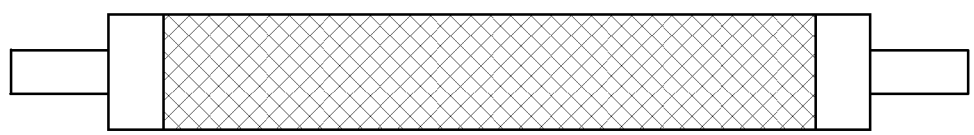
Figure 7A:
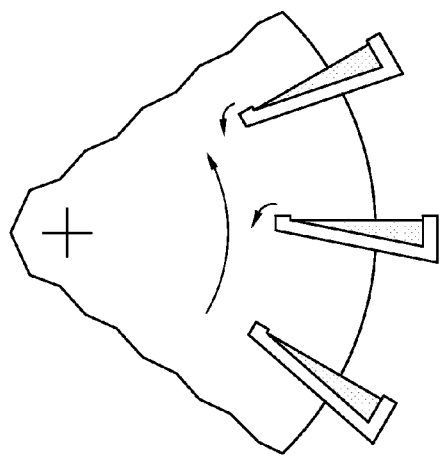
FIGS. 7A to 7D: These show transverse cross-sectional views of paddle structures illustrate options for refining the role and functions of paddles/other mixing structures and showing, respectively, in FIG. 7A paddle structures with overflow over the inner edge on rotation.
Figure 7B:
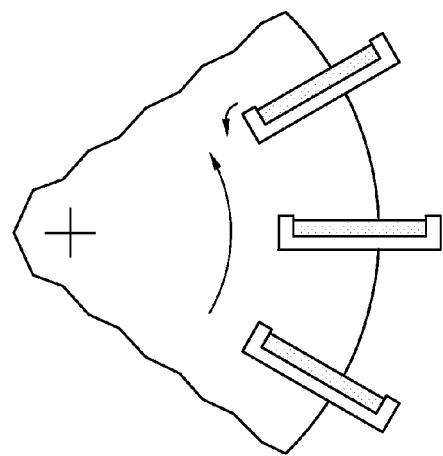
Figure 7C:
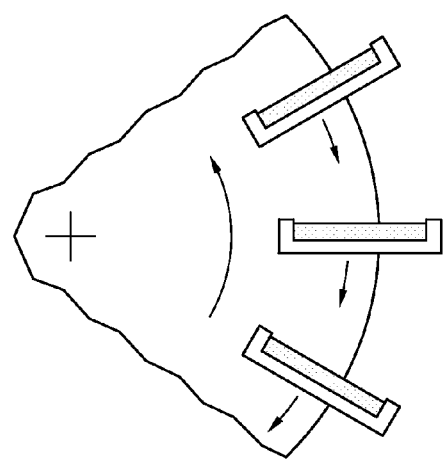
Figure 7D:
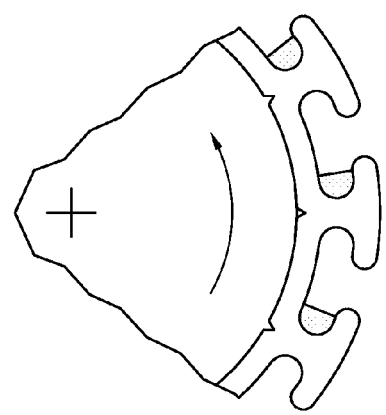
Figure 8A:
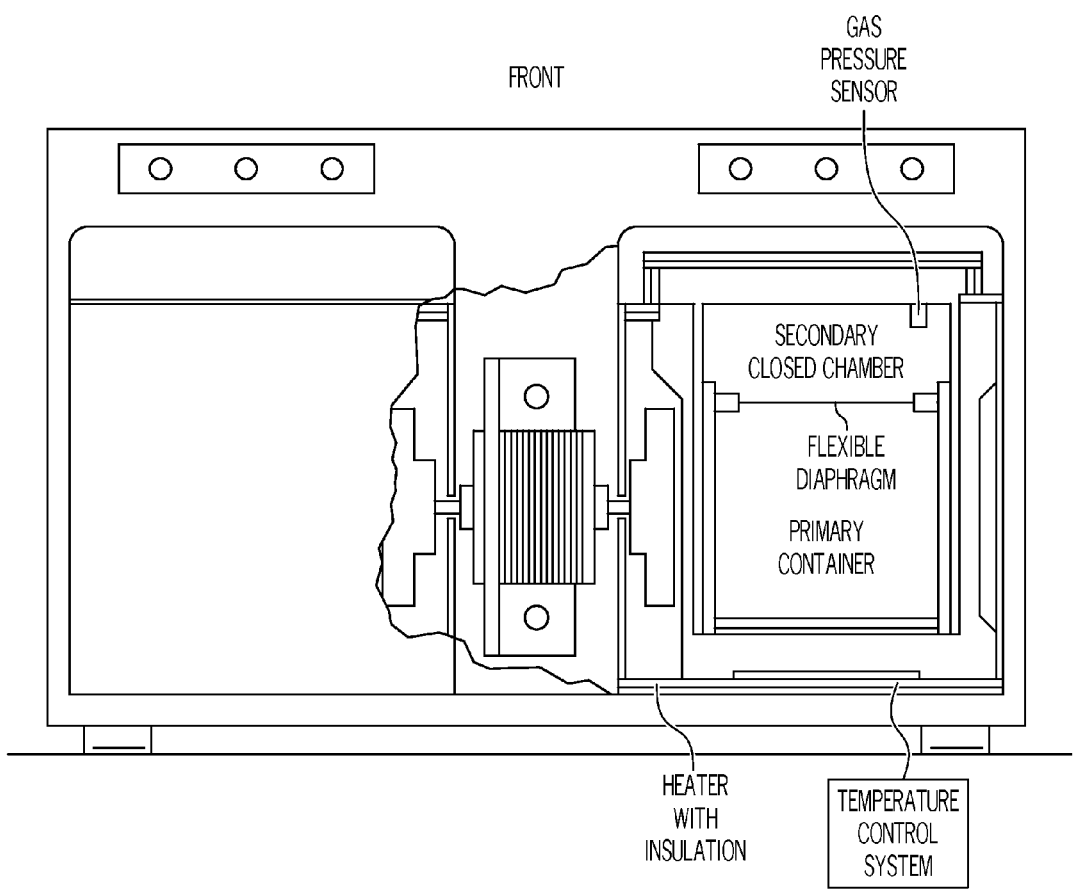
FIGS. 8A to 8B: The instrument in front view (8A), with a cutaway section to illustrate silo construction and operation of the central magnetic drive. Also a side view (8B) to illustrate scale and proportions.
Figure 8B:
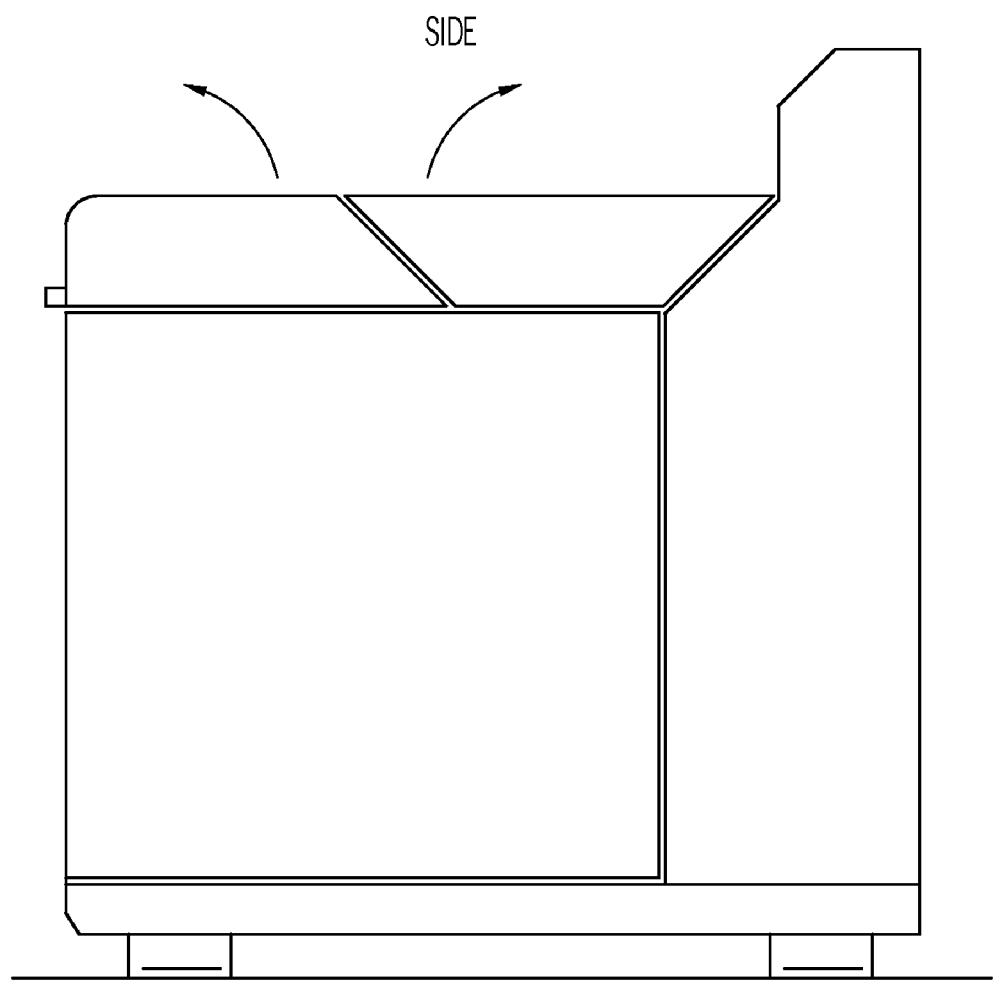

The majority of culture containers used as closed vessels are based on bottles, tubes or flasks generally of a robust grade of glass. The emphasis in this invention is upon the promotion of gas exchange, including a mixing means as a key feature. For this reason, and influenced by the format of the mixing means, the vessel is moulded as a trough, of approximately cuboid dimensions, with the lower half having a semicircular section. Within this, and closely following the wall profile, is a cylindrical mixing means. Since robustness is desirable the preferred material is polycarbonate. The working volume of the container is in the region of 125 ml., where 25 ml is headspace atmosphere and 100 ml. is the liquid phase. The container starts with a media volume of 90 ml. so that up to 10 ml of sample can be added. This ratio of volumes achieves a 1 in 10 dilution which is particularly advantageous in diluting antibiotics or inhibitors and rarely, if ever, provided in commercial systems. Biological materials, including cells and micro-organisms, will utilise and/or generate gases in the liquid phase. The resulting ingredients, if adequately mixed, will cause interaction with the headspace atmosphere and lead to variations on pressure. Metabolic activity can thus be monitored, and increases in cell numbers (by growth) cause corresponding increases in gas exchange.

In the specific embodiment the mixing means is a rotating structure such as a paddle wheel, designed to rotate and cause consistent disturbance to the liquid surface. This is analogous to a constant vortex, essentially improving the interfacial area and promoting gas exchange. Paddle blades leaving and re-entering the liquid phase cause useful disturbance. Paddle blades moving in the liquid phase assist mixing and uniformity of conditions. The rotating structure has a central shaft, the ends of which rotate in simple, plain bearing bushes—in this way the total mixing means follows a defined circular path about a relatively low friction mounting.

In addition to the basic structure the rotating element carries two small cylindrical ferrite magnets. This is the basis for a magnetic coupling to two external rare earth high power magnets. When the external magnets are rotated by a stepping motor drive, the internal paddle wheel rotates at exactly the same rate. Since the magnetic coupling operates through the wall of the vessel there are no seals, apertures or other potential leakage points. A simple magnetic steering in the form of a rotating bar in a cylindrical bottle is described in WO9402238, but here the mixing action is created by the magnet per se, usually rotating at approximately 200 rpm. The arrangement described in this invention operates at substantially slower speeds and the magnetic coupling is precisely aligned in a 'captive' registration of the magnets.

In one aspect, the container includes a mixing means to promote gas exchange between the liquid phase and gaseous phase, in which the mixing means is driven indirectly (for example, magnetic coupling).

Within the general arrangement there is scope for shaped blades, and blades with apertures/slots to carry fluid clear of the surface to trickle back into the main volume (thereby presenting additional liquid/gas interfase area). There is also scope for variations in speed and direction, including intermittent movement at defined intervals.

The central axle, which rotates at the same rate as the peripheral paddles, is exposed to minimal shear forces but does come into contact with a major proportion of the liquid phase. This offers a route for support surfaces to encourage growth on carrier materials, or addition of growth factors eluted from the surface, (or conversely the removal of antibiotics/inhibiters which otherwise prevent/reduce active growth).

Normal operation of the paddle wheel achieves the primary role of 'mixing means', while also providing options for several secondary functions. While magnetic couplings are well established in pumps and other devices, the incorporation of a specific structure, driven by a suitable coupling, is novel in a closed culture vessel assembly.

Intermittent operation of the drive is possible and may have advantages with some cultures (for example where growth of a pellicle is to be encouraged, or simply to limit mechanical damage to fragile cells).

The vessel described so far is completed as an assembly by the addition of a "lid" as a closure. The "lid" has a series of features built into the structure which provide additional function. For the purposes of this invention, the first of these functions is a link to the main vessel headspace from a secondary chamber of approximately 5 ml capacity. The central feature is a working diameter of 25-30 mm, across which a flexible diaphragm membrane is mounted. The diaphragm provides a containment barrier, whilst allowing pressure variations across the interface between primary and secondary chambers. Diameter, thickness and flexibility can be varied, but the most consistent requirement is that the diaphragm membrane is totally impermeable to gases. In practical use, the culture vessel, with integral diaphragm, is treated as a one-use disposable. For this reason a resilient seal (eg. made of rubber) on the container has a formation designed and adapted to receive and locate a "boss" on the sensor assembly which is part of the instrument.

In a simplified, non-electronic, version of the pressure sensor, use is made of a fluid-filed manometer tube with a flexible membrane at the base end. This membrane is physically linked to that of the culture vessel (using a magnetic link or a small area of "hook and loop fastener" (eg. Velcro™) so that the two membranes move as one. Hence fluid is moved in the manometer for visual observation.

A culture container in transit may be shaken or inverted. Consequently the pressure transfer link to the headspace is closed until required, thus avoiding the ingress of fluids into critical regions of the lid assembly. This is easily achieved by a small area foil seal, perforated on demand by pressure on a hollow pin with a sharp, cutting action end. To preserve sterility this action can be performed indirectly via a flexible covering membrane.

A similar valve action, or equivalent opening of a rubber seal mechanism, can be provided to open a link to a barrier filter venting to the surroundings. The filter must be totally effective in preventing the escape of both bacteria and viruses. Since many cultures, particularly anaerobic bacteria, are capable of establishing appreciable pressures this is a basis for a pressure relief device which operates automatically or on demand. In a preferred version automatic operation is initiated by gas pressure directly, which is fail/safe. On demand operation is controlled by the instrument electronically, and can be triggered for both excess positive pressure or persistent negative pressure.

There is a further function involving valve operation linked to a filter protected port to atmosphere. Equilibration to atmospheric pressure can be carried out at any time to effectively zero the pressure sensor. In particular this is a useful facility during injection of a sample; opening a port allows progressive displacement of headspace gas to accommodate the incoming volume of sample. In conventional bottle based systems it is usual to have a partial vacuum to allow ingress of sample, thus avoiding pressurization which is dangerous and undesirable. In contrast this invention matches displacement to sample volume exactly. This has an advantage where the incoming volume is large. Valve operation should again be indirect, via a membrane barrier, to maintain integrity of the culture vessel.

Finally it is usual to inject samples using a septum pierced by a hypodermic needle/syringe. In this case the septum should be of minimal diameter and relatively thick material, to avoid any barometric influence. Once the needle is retracted it is essential that the septum material has excellent characteristics. In view of the characteristics of the injection port it is highly desirable that sample addition or removal is the specific function for which it is used. The culture container as described avoids the incorporation of any components or materials which would be classified as "sharps". The only operation using a conventional needle is sample addition (or removal for subculture/staining). The region of the lid, directly over the injection septum, is essential for access.

For this reason the lid includes a chimney-like formation which encircles the needle and provides some shielding of the technicians using the culture units. The possibility of needle stick injuries should be reduced by correct use of this feature. The outer end of the access tube will initially be closed by a cap with integral tamper-evident seal. The cap can be reapplied but provides a clear indication that a culture unit has been partially opened or inoculated.

The lid assembly is a composite unit, housing several features, which could be a 'sandwich' construction where the 'filling' is a moulded rubber membrane showing different features in different areas. The outer casework can be coded in various ways to identify contents and application. This can include colour coding with or without labelling, possibly bar coding as a computer compatible identification code.

The smaller components (foil seals, perforators and filter elements) are assembled into the lid casing prior to closure and bonding into the vessel, followed by gamma irradiation to sterilise the complete assembly.

An aspect of the culture vessel design is the selection of appropriate materials.
Avoidance of "sharps" and widely diverse materials is intended to simplify final disposal after use. For safety reasons terminal autoclaving is advisable; this would be followed by combustion using methods normally employed for disposables.
Conventional culture containers create difficulties in disposal; the use of appropriate materials is intended to improve the environmental impact of large scale usage and disposal.

In one aspect, the container, with associated components, contents, and pressure transfer diaphragm is made from materials selected for effective and environmentally sound disposal.

The durable part of the culture system takes the form of a compact, dedicated instrument. In typical applications (eg Blood culture) the instrument has a capacity of two culture units (usually one aerobic/one anaerobic). The culture units are each housed in a incubation"silo". The pressure sensing system will register the effect of temperature change; indeed the progression from room temperature to incubation temperature (37°) produces a marked rise in pressure. This is a useful indication that the instrument is working well and that there are no leaks at the connection between disposable and instrument. The silo wall is close to the disposable vessel and almost all heat transfers by radiation. The air layer slows heat transfer but this also applies to losses and thus has a stabilising effect. Particular attention is applied to extensive insulation using eg. Nomex™ card. This may also block air currents and any uncontrolled losses. It is relatively easy to control temperatures with tight precision and confer good stability on the system. Individual test vessels may get individual control and are not prone to temperature variation. If necessary the bottom of the silo may be fitted with a pair of electrodes so that, in the very unlikely event of a leakage a warning light is illuminated. Under such circumstances the complete silo and culture vessel is removed for sterilisation without risk of uncontrolled leakage.

In one aspect of the invention, the pressure sensing system has precise temperature control using a small, low wattage heater pad bonded to the external surface of the silo, linked to a safety thermostat and subject to constant monitoring.

In a preferred version of the magnetic drive, a double ended rotor has a motor on both shafts with high power Neodymium Boron magnets mounted in each rotor. The two "silos" are addition (or removal for subculture/staining). The region of the lid, directly over the injection septum, is essential for access.

For this reason the lid includes a chimney-like formation which encircles the needle and provides some shielding of the technicians using the culture units. The possibility of needle stick injuries should be reduced by correct use of this feature. The outer end of the access tube will initially be closed by a cap with integral tamper-evident seal. The cap can be reapplied but provides a clear indication that a culture unit has been partially opened or inoculated.

The lid assembly is a composite unit, housing several features, which could be a 'sandwich' construction where the 'filling' is a moulded rubber membrane showing different features in different areas. The outer casework can be coded in various ways to identify contents and application. This can include colour coding with or without labelling, possibly bar coding as a computer compatible identification code.

The smaller components (foil seals, perforators and filter elements) are assembled into the lid casing prior to closure and bonding into the vessel, followed by gamma irradiation to sterilise the complete assembly.

An aspect of the culture vessel design is the selection of appropriate materials.
Avoidance of "sharps" and widely diverse materials is intended to simplify final disposal after use. For safety reasons terminal autoclaving is advisable; this would be followed by combustion using methods normally employed for disposables.
Conventional culture containers create difficulties in disposal; the use of appropriate materials is intended to improve the environmental impact of large scale usage and disposal.

In one aspect, the container, with associated components, contents, and pressure transfer diaphragm is made from materials selected for effective and environmentally sound disposal.

The durable part of the culture system takes the form of a compact, dedicated instrument. In typical applications (eg Blood culture) the instrument has a capacity of two culture units

EXAMPLE

Operation as a Blood Culture System

1. Select two disposable culture vessel units, one aerobic and one anaerobic. The growth media is based on Trypticase Soy Broth with supplementary nutrients. The anaerobic version includes reducing agents to form an oxygen free state. Aerobic media has a headspace gas of air, if for immediate use, or oxygen enriched, if held in store for a long duration. In contrast the gas for an anaerobic state is Nitrogen with 10% Carbon Dioxide and 1% Hydrogen.
2. Collect a blood sample of a maximum of 20.0 mls.
3. Remove the tamper-evident closure from each unit (vested) and swab the rubber septum area.
4. Inoculate with up to 10 ml. per vessel, while depressing the pressure balance valve, allowing displaced headspace gas to escape via a filter.

5. Prepare to load both containers into the instrument, which should be already at the working temperature. Load and activate connection valve from headspace to sensor chamber on both vessels.
6. Check magnetic drive operational and monitor pressure warm-up curve (note: the algorithm is automatically inhibited during this period of rapid change.)
7. Incubation continues for a maximum of seven days; generally most positive results are flagged well within 24 hours (eg 10 hours).
8. Positive cultures are detected by the algorithm and "flagged" by a warning LED on top of the instrument.
9. In some cases pronounced positive pressure, or ongoing negative, reducing pressure is detected and the controller actuates a venting valve (to return the unit to atmospheric pressure via a filter element).
10. The laboratory operator removes positive culture for sub-culture and further tests, or negatives which have completed the full term of incubation to go to disposal.

The invention claimed is:

1. Apparatus for non-invasive monitoring of gas exchange by biological material suitable for non-expert use in a non-laboratory setting, wherein the apparatus comprises:
   a primary sealed container;
   wherein said primary sealed container includes a liquid-gas mixer to promote gas exchange between liquid phase contents and gaseous phase contents of said primary sealed container, and
   wherein said primary sealed container and the contents of said primary sealed container are a single-use, disposable item;
   a temperature control system; and
   an indirect gas pressure sensing system for non-invasive monitoring of gas pressure in said primary sealed container;
   wherein the indirect as pressure sensing system comprises:
   a secondary chamber;
   a non-biologically toxic gas impermeable flexible diaphragm;
   wherein the diaphragm is located between the primary sealed container and the secondary chamber to communicate pressure changes within the primary sealed container to the secondary chamber, wherein the diaphragm is mechanically free to respond to both negative and positive pressure changes, and wherein the diaphragm forms a barrier isolating the secondary chamber from the contents of the primary sealed container; and
   a gas pressure sensor;
   wherein the secondary chamber defines a sealed, gas-tight secondary volume; and
   wherein the gas pressure sensor is located within the sealed, gas-tight secondary volume;
   wherein the gas pressure sensor is isolated from changes in barometric pressure and able to detect a negative pressure in which a pressure within the primary sealed container is less than a pressure within the sealed, gas-tight secondary volume; and
   wherein there is a defined relationship between the primary and secondary pressures, which permits the pressure sensor in the secondary chamber to generate a signal representing primary pressure in the sealed container and remain isolated from the contents of the primary sealed container.

2. A pressure sensing system according to claim 1, wherein the pressure sensor provides electrical outputs representing the pressure detected, and the outputs are fed to data processing means capable of producing a measurement of primary pressure.

3. The pressure sensing system according to claim 2, wherein the signals include identity codes for identification of the container, pressure sensing unit and data processing means.

4. The apparatus according to claim 1, having a primary sealed container partially filled with liquid, wherein pressure variations are in the gaseous phase of the headspace of the primary sealed container due to biological activity with the liquid.

5. The apparatus according to claim 1 having a liquid culture of cellular material partially filling the primary sealed container.

6. The apparatus according to claim 5, wherein the cellular material is micro-organisms, plant tissue cells, or animal cells.

7. The apparatus according to claim 5 wherein metabolism and/or growth of the cellular material causes as exchanges between liquid and headspace, which result in primary pressure changes.

8. The apparatus according to claim 1, further comprising a frangible seal that can only be broken by a hollow component pushed into place via indirect pressure on a flexible covering, thereby creating an irreversible valve action.

9. The apparatus according to claim 1, wherein the primary sealed container comprises a first opening to headspace of the container and a second opening to the external atmosphere such that a connection is made on the application/removal of the pressure, exerted indirectly via flexible covering, whereby the container contents can assume atmospheric pressure as and when necessary, and whereby this can be operated at any time.

10. The apparatus according to claim 9, wherein the second opening to the external atmosphere is via a filter.

11. The apparatus according to claim 10, wherein the second opening further comprises either a second route to the filter or a separate filter to provide a venting port, which is activated if the container headspace becomes either positive or negative to pressure.

12. The apparatus according to claim 1, wherein the primary sealed container comprises a fluid transfer septum for addition or removal of the contents of the sealed container.

13. The apparatus according to claim 12, further comprising a tamper-evident closure for the point of access to the container, and a physical formation which extends above the septum so that the latter is at the base of a recess, so as to limit the possibility of a needle-stick injury to an operator using the system.

14. The apparatus according to claim 1, wherein the single use disposable item includes batch and application specific data in the form of a bar code label.

15. The apparatus according to claim 1, wherein the single-use disposable item comprises colour coding of the top or other prominent region of the container.

16. An apparatus according to claim 1, wherein the entire disposable item is located in a temperature controlled silo, thereby stabilizing the temperature.

17. The apparatus according to claim 16, wherein the silo, is insulated, thereby minimizing heat losses.

18. The apparatus according to claim 16, wherein the system has temperature control using a heating pad bonded to the external surface of the silo, linked to a safety thermostat.

19. A single test unit for use in the apparatus according to claim 1, comprising a temperature controlled silo, a magnet drive rotor attached to a motor, a pressure sensor assembly and a micro processor which controls and monitors pressure, wherein the processor can apply a predetermined algorithm to make interpretations and display status and outcomes to human operators.

20. The single test unit according to claim 19, wherein groups of a single test unit/dual test unit form a compact array so as to provide a test facility which can be scaled up.

21. A test unit for use in the apparatus according to claim 1, comprising two silos, two sensor systems and one double ended motor carrying two magnetic drive rotors and a micro processor dealing with data, whereby two tests, usually from one sample, can be run simultaneously.

22. A test unit for use in the apparatus according to claim 1, wherein the unit provides monitoring a plurality of test containers, wherein each single dual arrangement is serviced by its own pressure sensing system and wherein each system reports its findings and conclusions to a centralized and/or remote location, in conjunction with an ID code which denotes the locations of the system/test combinations.

23. The apparatus according to claim 1, wherein the mixing means is driven indirectly.

24. The apparatus according to claim 23, wherein the mixing means is driven indirectly by magnetic coupling.

25. The apparatus according to claim 1, wherein the mixer is a rotating component and wherein the rotating component includes paddles, hollow paddles, perforated paddles, or cylindric forms it pockets, recesses or holes.

26. The apparatus according to claim 1, further comprising a system to manage pressure within said primary sealed container.

27. A method for non-invasive monitoring of gas exchange by biological material, the method comprising;
providing an indirect pressure sensing system for non-invasive measurement of primary pressure in a sealed container, wherein the pressure sensing system comprises a primary sealed container, and a secondary chamber;
providing a gas pressure sensor;
isolating the secondary chamber and pressure sensor from the primary sealed container contents using a non-biologically toxic gas impermeable flexible diaphragm as a barrier;
communicating primary pressure changes from within the primary sealed container via said diaphragm;
enabling said diaphragm to move in response to both positive and negative pressure changes;
establishing a defined relationship between the primary and secondary pressures;
generating a signal representing primary pressure in the primary sealed container using the pressure sensor in the secondary chamber whilst maintaining isolation of said pressure sensor from the contents of the primary sealed container;
controlling a temperature of said pressure sensing system to control variations in said primary pressure;
maintaining a pressure within said primary sealed container of approximately atmospheric pressure;
sensing both positive and negative pressure changes of less than one atmosphere;
partially filling said primary sealed container with liquid using said pressure sensor; and
exchanging headspace gas in said primary sealed container with said liquid, such that sensed pressure variations arise in the gaseous phase of the headspace of the primary sealed container due to biological activity within the liquid;
wherein the secondary chamber defines a sealed, gas-tight secondary volume; and
wherein the gas pressure sensor is provided within the sealed, gas-tight secondary volume.

* * * * *